United States Patent
Nolan et al.

(10) Patent No.: US 9,821,166 B2
(45) Date of Patent: Nov. 21, 2017

(54) INDICATION OF COUPLING BETWEEN MEDICAL DEVICES

(75) Inventors: Joseph J Nolan, Minnetonka, MN (US); Andrew H. Houchins, Lino Lakes, MN (US)

(73) Assignee: Medtronic, Inc., Minneapolis, MN (US)

( * ) Notice: Subject to any disclaimer, the term of this patent is extended or adjusted under 35 U.S.C. 154(b) by 1790 days.

(21) Appl. No.: 12/127,404

(22) Filed: May 27, 2008

(65) Prior Publication Data

US 2009/0299438 A1  Dec. 3, 2009

(51) Int. Cl.
*A61N 1/08* (2006.01)
*A61N 1/372* (2006.01)

(52) U.S. Cl.
CPC ............ *A61N 1/37211* (2013.01); *A61N 1/08* (2013.01)

(58) Field of Classification Search
CPC .................................................. A61N 1/37211
USPC ............................................. 607/60, 32, 57
See application file for complete search history.

(56) References Cited

U.S. PATENT DOCUMENTS

| | | | |
|---|---|---|---|
| 5,584,869 A * | 12/1996 | Heck et al. | 607/57 |
| 5,824,022 A * | 10/1998 | Zilberman | A61N 1/36032 128/903 |
| 6,516,227 B1 | 2/2003 | Meadows et al. | |
| 6,574,511 B2 | 6/2003 | Lee | |
| 6,738,671 B2 | 5/2004 | Christophersom et al. | |
| 6,978,181 B1 | 12/2005 | Snell | |
| 7,076,303 B2 | 7/2006 | Linberg | |
| 7,110,823 B2 | 9/2006 | Whitehurst et al. | |
| 7,177,700 B1 | 2/2007 | Cox | |
| 7,218,969 B2 | 5/2007 | Vallapureddy et al. | |
| 2002/0072785 A1 * | 6/2002 | Nelson | A61B 5/0031 607/60 |
| 2002/0123778 A1 | 9/2002 | Linberg | |
| 2003/0060859 A1 | 3/2003 | Bourget | |
| 2004/0064166 A1 * | 4/2004 | Thompson | A61N 1/37252 607/60 |
| 2005/0137653 A1 | 6/2005 | Friedman et al. | |
| 2005/0245992 A1 | 11/2005 | Persen et al. | |
| 2005/0251228 A1 | 11/2005 | Hamel | |
| 2006/0020302 A1 | 1/2006 | Torgerson et al. | |

(Continued)

FOREIGN PATENT DOCUMENTS

WO  WO 01/32261 A1  5/2001

OTHER PUBLICATIONS

U.S. Appl. No. 11/800,423, filed May 4, 2007, entitled "Intelligent Discovery of Medical Devices by a Programming System."

(Continued)

*Primary Examiner* — Alyssa M Alter
(74) *Attorney, Agent, or Firm* — Shumaker & Sieffert, P.A.

(57) ABSTRACT

Techniques for providing an indication of coupling between medical devices are disclosed. For example, when a programming device and a telemetry module are coupled, the telemetry module provides a first indication, and the programming device provides a second indication substantially similar to the first indication. The indications may be, for example, colors, and different indications may signify communication with different implantable medical devices, programming different therapies, or use of different applications of the programming device.

27 Claims, 10 Drawing Sheets

(56) References Cited

U.S. PATENT DOCUMENTS

2006/0161213 A1 7/2006 Patel
2006/0224213 A1 10/2006 Fuller et al.

OTHER PUBLICATIONS

"N'Vision® Clinician Programmer with Software," User Manual, Apr. 2007.
Notification of Transmittal of the International Search Report and the Written Opinion of the International Searching Authority, or the Declaration dated Nov. 5, 2009 for corresponding PCT Application No. PCT/US2009/044876 (16 pgs.).

* cited by examiner

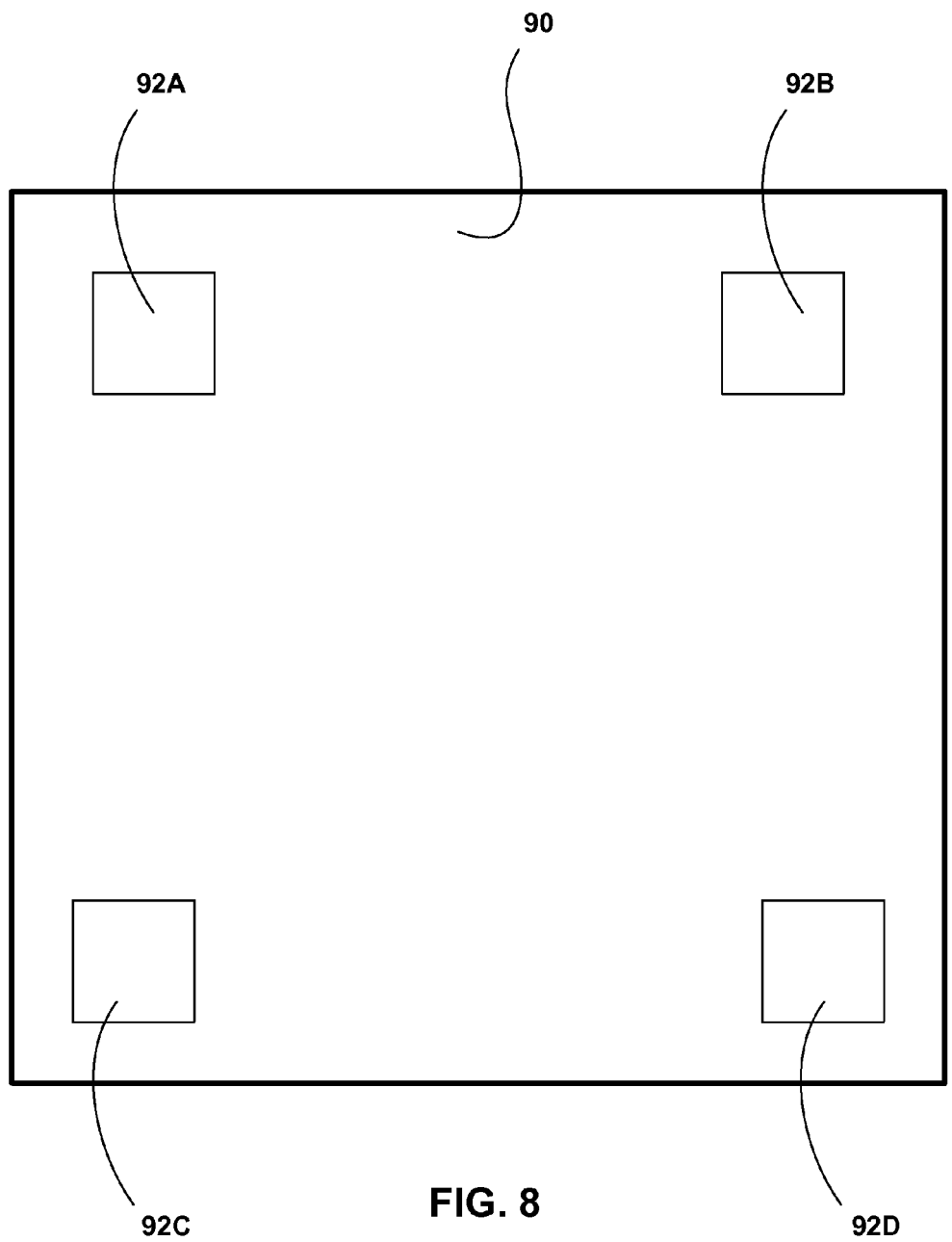

1

INDICATION OF COUPLING BETWEEN MEDICAL DEVICES

TECHNICAL FIELD

The invention relates to medical devices and, more particularly, to medical device communication.

BACKGROUND

Implantable medical devices, such as electrical stimulators or therapeutic agent delivery devices, may be used to deliver electrical stimulation therapy to patients to treat a variety of symptoms or conditions such as chronic pain, tremor, Parkinson's disease, epilepsy, urinary or fecal incontinence, sexual dysfunction, obesity, mood disorders (e.g., depression), other psychiatric disorders (e.g., obsessive-compulsive disorder), gastroparesis or diabetes. In some cases, the electrical stimulation may be used to stimulate muscles, e.g., provide functional electrical stimulation (FES) to promote muscle movement or prevent atrophy. A patient may have more than one implantable medical device implanted to alleviate the variety of symptoms.

Generally, a clinician, e.g., physician, uses an external programming device to communicate with an implantable medical device. The clinician may use the external programming device to, for example, program the therapy delivered by the implantable medical device, or retrieve physiological or diagnostic information collected by the implantable medical device. Furthermore, a patient may use an external programming device to communicate with his or her implantable medical device, e.g., for control of therapy or to receive physiological or diagnostic messages.

External programming devices communicate with implantable medical devices transcutaneously using, for example, radio frequency of near-field magnetic communication techniques. Typically, external programming devices have been coupled by a cable to a telemetry head comprising an antenna for communication with implantable medical devices. The telemetry head is positioned over or very near the implantable medical device, with the cable enabling the programming device to be used a comfortable distance from the patient.

SUMMARY

In general, the disclosure describes techniques for indicating coupling between medical devices. In some examples, a system comprises an implantable medical device, an external telemetry module, an external programming device, and an application executed by the programming device for communication with the implantable medical device, e.g., for programming a particular therapy delivered by the implantable medical device. The telemetry module transcutaneously communicates with the implantable medical device, and the programming device communicates with the telemetry module and, through the telemetry module, with the implantable medical device. In some examples, the telemetry module is not physically connected to the external programming device and wirelessly communicates with the programming device.

There may be a plurality of implantable medical devices implanted within a patient or otherwise within a range of communication of the telemetry module. Furthermore, one or more implantable medical devices may provide a plurality of different therapies or monitoring functions, and a programming device may execute different applications for programming or retrieving data from different implantable medical devices or for different therapies or monitoring functions. Additionally, there may be multiple programming devices and telemetry modules in proximity, e.g., in range of communication with each other or with the implantable medical devices, and there may be multiple users of such external devices.

The disclosure provides techniques for indicating which application, programming device, telemetry module, implantable medical device, and therapy are currently coupled, or being used or programmed, in such a system. In some embodiments, one or more system elements may further indicate which user or user preferences are active. Indicating coupling between devices may include indicating bonding, e.g., a logical connection facilitating secure communication, or actual communication between the devices.

For example, a telemetry module may be configured to provide a plurality of different indications, each indication indicating at least one of coupling to a particular implantable medical device, programming of a particular therapy, or use of a particular application by the programming device. The different indications may be different colors provided by, for example, a plurality of lights, e.g., light emitting diodes. The lights may be located within a housing of the telemetry module, a non-display portion of which may be translucent to allow the light, which may be colored, to emit through the housing. In other examples, the different indications may be audible or tactile. In some examples, the different indications may comprise different temporal or spatial patterns, and the patterns may be one or more of sound, light, vibration or animation. In some examples, the telemetry module does not include the display, or the indications are otherwise provided without the use of the display.

In some examples, when a programming device and a telemetry module are coupled, the telemetry module provides a first indication, and the programming device provides a second indication substantially similar to the first indication. In this manner, the programming device and telemetry module may indicate their coupling. The programming device may provide a substantially similar indication via its display, such as by providing a color in a background, application window, or other icon on the display that is substantially similar to the indication provided by the telemetry module.

A user of the programming device and telemetry module may want to insure that the programming or other interactions they have with an implantable medical device are with the intended device, for example, to avoid misprogramming an implantable medical device. Confusion as to which implantable medical device is being communicated with, or which telemetry module or application is needed to communicate with a particular implantable medical device or program a particular therapy or other function of the implantable medical device, may result in problems, including wasted user time and user frustration. Devices configured to provide a plurality of indications in accordance with this disclosure may allow a user to avoid such problems.

In some examples, the user may associate particular indications with particular devices, therapies, or applications, as well as with his or herself as a user. An association may be made, for example, when bonding devices or first using a particular application. In this manner, the user may be provided user-specific indications that are more likely to be remembered by the user.

In one example, the disclosure is directed to a system comprising an external telemetry module that transcutaneously communicates with an implantable medical device and an external programming device that communicates with the telemetry module and with the implantable medical device through the telemetry module. When the telemetry module and the programming device are coupled, the telemetry module provides a first indication of coupling and the programming device provides a second indication of coupling that is at least substantially similar to the first indication.

In another example, the disclosure is directed to a method for indicating coupling between an external telemetry module that transcutaneously communicates with an implantable medical device and an external programming device that communicates with the telemetry module and with the implantable medical device through the telemetry module. The method comprises, when the telemetry module and programming device are coupled, providing a first indication of coupling via the telemetry module, and providing a second indication of coupling via the programming device. The first and second indications are at least substantially similar.

In another example, the disclosure is directed to a system comprising means for transcutaneously communicating with an implantable medical device, and programming means for communicating with the implantable medical device through the means for transcutaneously communicating with an implantable medical device. The means for transcutaneously communicating comprises means for providing a first indication of coupling with the programming means. The programming means comprises means for providing a second indication of coupling with the means for transcutaneously communicating. The first and second indications are at least substantially similar.

In another example, the disclosure is directed to a telemetry module comprising a housing, wherein at least ten percent of a non-display portion of the housing is translucent. The telemetry module further comprises communication circuitry within the housing, the communication circuitry configured for communication with programming devices and transcutaneous communication with implantable medical devices to enable transcutaneous communication between the programming devices and the implantable medical devices, and a plurality of lights within the housing that are visible through at least the translucent portion of the housing and that provide a plurality of different colors to indicate to which of the programming devices or implantable medical devices the telemetry module is coupled.

In another example, the disclosure is directed to a displayless telemetry module comprising communication circuitry configured for wireless communication with a plurality of medical devices, and at least one non-display indicator to provide a plurality of coupling indications to a user, each coupling indication indicating coupling to a respective one of the plurality of medical devices.

BRIEF DESCRIPTION OF DRAWINGS

FIG. 8 is a schematic diagram illustrating an example telemetry module.

DETAILED DESCRIPTION

Figure 1:
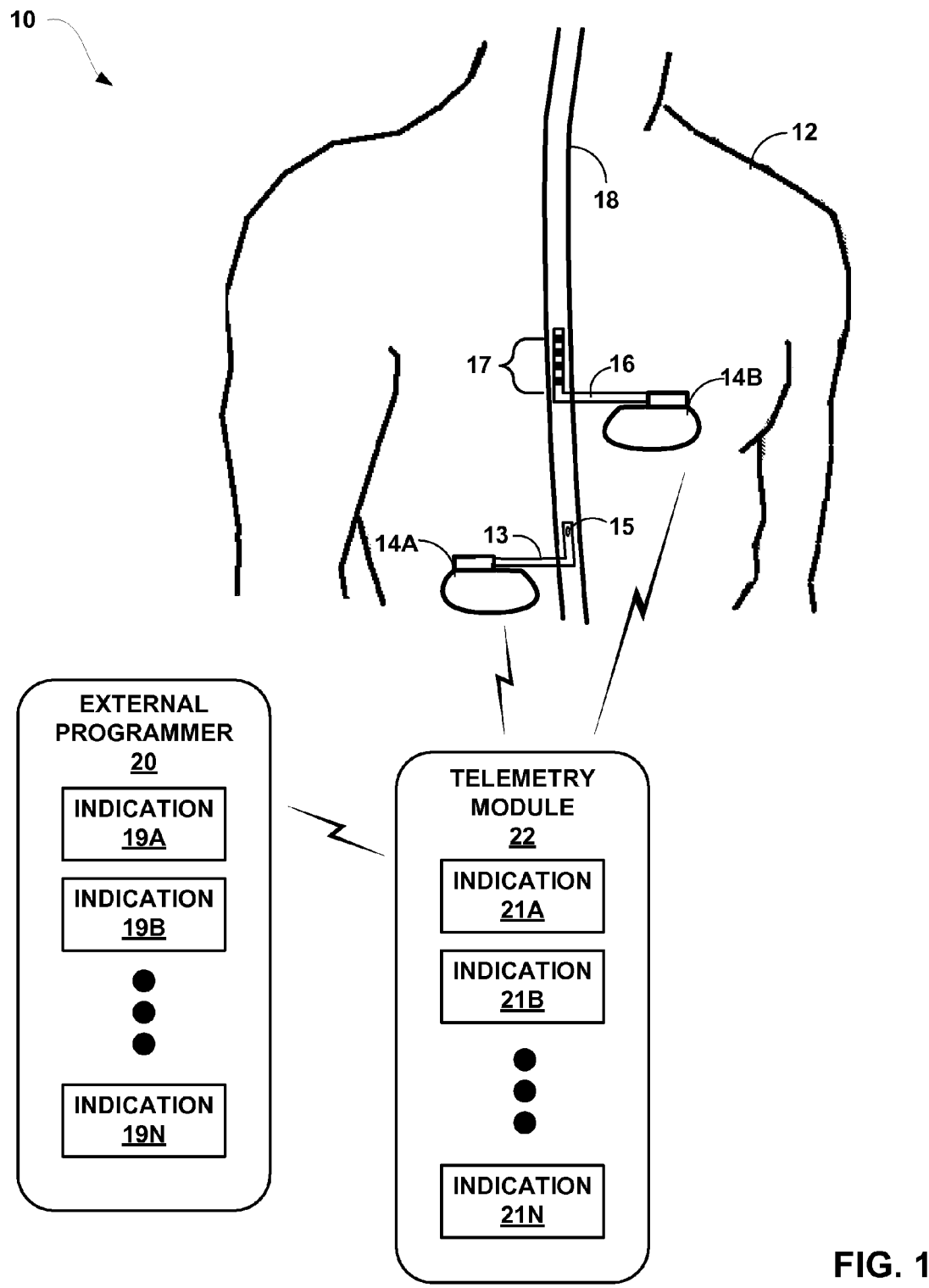
FIG. 1 is a conceptual diagram illustrating an example system in which devices provide coupling indications.

FIG. 1 is a conceptual diagram illustrating an example system 10 in which devices provide coupling indications. System 10 includes implantable medical device (IMD) 14A and IMD 14B (collectively "IMDs 14") implanted within a patient 12. In the illustrated example, IMD 14A comprises an implantable pump for delivery of a therapeutic substance proximate to spinal cord 18 of patient 12, e.g., within the epidural or intrathecal space, via catheter 13 and port 15. In the illustrated example, IMD 14B comprises an implantable stimulator that delivers electrical stimulation to spinal cord 18 via a plurality of electrodes 17 on a lead 16. In the illustrated example, IMDs 14 are implanted on respective sides of patient 12.

The numbers and locations of IMDs 14, catheter 13, port 15, lead 16, and electrodes 17 are merely examples. In various examples, systems may include any number of IMDs, coupled to or comprising any number or type of therapy delivery and/or sensing elements, for providing any type of therapy and/or patient monitoring. Patient 12 will ordinarily be a human patient. In some cases, however, the invention may be applied to non-human patients.

As shown in FIG. 1, system 10 may also include an external programming device, e.g., external programmer 20 that provides a user interface and software applications for interacting with IMDs 14. For example, a clinician or patient may program infusion parameters for IMD 14A and stimulation parameters for IMD 14B, or receive diagnostic or physiological data from the IMDs. Programmer 20 may comprise, as examples, a handheld device, tablet or other portable computer, personal computer, or workstation. Programmer 20 may be a custom device dedicated to interacting with IMDs, or a general-purpose computing device configured to running application software for interacting with IMDs.

System 10 also includes a telemetry module 22, which facilitates communication, e.g., acts as a communication link, between programmer 20 and IMDs 14. In particular, telemetry module 22 is configured for transcutaneous communication with IMDs 14 and, in the illustrated example, wireless communication with programmer 20. In some examples, telemetry module 22 is physically coupled to programmer 20, e.g., via a cable. Telemetry module 22 may be a hand-held device that, in some examples, unlike programmer 20, does not include a display.

As illustrated in FIG. 1, external programmer 20 is configured to provide a plurality of different indications 19A-19N (collectively "indications 19"). In the illustrated example, telemetry module 22 is also configured to provide a plurality of indications 21A-21N (collectively "indications 21"). Programmer 20 and telemetry module 22 may respectively select and provide one or more of indications 19 and 21 at any given time to indicate one or more of the coupling of the programmer with the telemetry module, with which of IMDs 14 the programmer and telemetry module are communicating, which therapy or other functionality of the IMD 14 is being programmed or otherwise interacted with, or which application of programmer 20 is used to communicate with the IMD 14, as examples. In some examples, as will be discussed below, the IMD 14 with which programmer 20 and telemetry module 22 are coupled may also provide an indication, e.g., that it is the IMD to which the programmer and telemetry module are coupled, or what therapy or other functionality is being programmed or otherwise interacted with. Indicating coupling between devices, e.g., between an IMD and telemetry module or telemetry module and programmer, may include indicating bonding, e.g., a logical connection facilitating secure communication, or actual communication between the devices.

The different indications 19, 21 may comprise different colors. In some examples, at least three different colors are provided. The different colors may be provided by, for example, a plurality of light emitting diodes (LEDs) or other lights, or as colored elements of a display. In some examples, programmer 20 includes a display, while telemetry module 22 does not and utilizes lights to provide the different colors. The disclosure is not limited to such examples, however, and either device may include a display or lights, and utilize one or both of a display or lights to provide the different colors. In some examples, indications 19, 21 may additionally or alternatively be audible or tactile. Furthermore, in some examples, indications 19, 21 may comprise different temporal or spatial patterns, and the patterns may be one or more of sound, light, color, vibration, music, or animation.

In some examples, when programmer 20 and telemetry module 22 are coupled, they respectively select and provide indications 19, 21 that are substantially similar, e.g., include substantially similar colors. In this manner, programmer 20 and telemetry module 22 may indicate their coupling to a user. Programmer 20 and telemetry module 22 may be configured to provide a plurality of indications 19, 21 that are substantially similar, and which of the substantially similar indications is provided may be determined based on the IMD 14 with which the programmer and telemetry module are communicating, or an associated therapy or application of programmer 20, as described above.

Other example systems may include a plurality of programmers 20 and/or a plurality of telemetry modules 22. For example, a plurality of programmers 20 may, at the same or different times, communicate with respective ones of IMDs 14 via telemetry module. As another example, programmer 20 may, at the same time or different times, use respective telemetry modules 22 to communicate with each of IMDs 14.

Figure 2A:
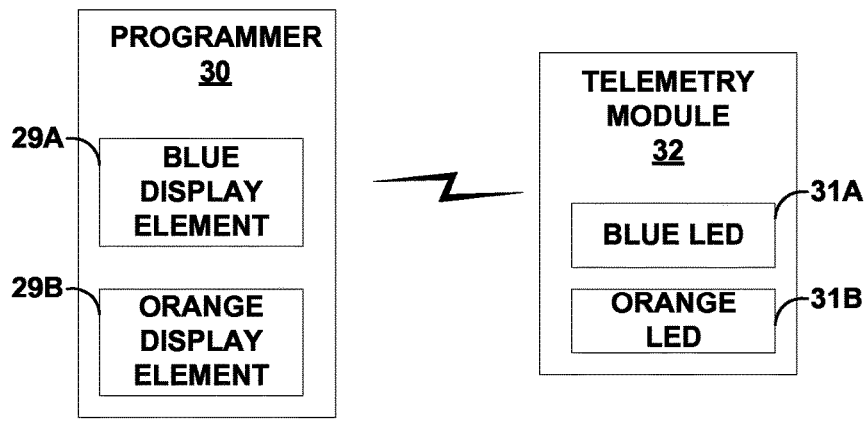
FIGS. 2A and 2B are conceptual diagrams illustrating example indications provided by a programming device and telemetry module.
Figure 2B:
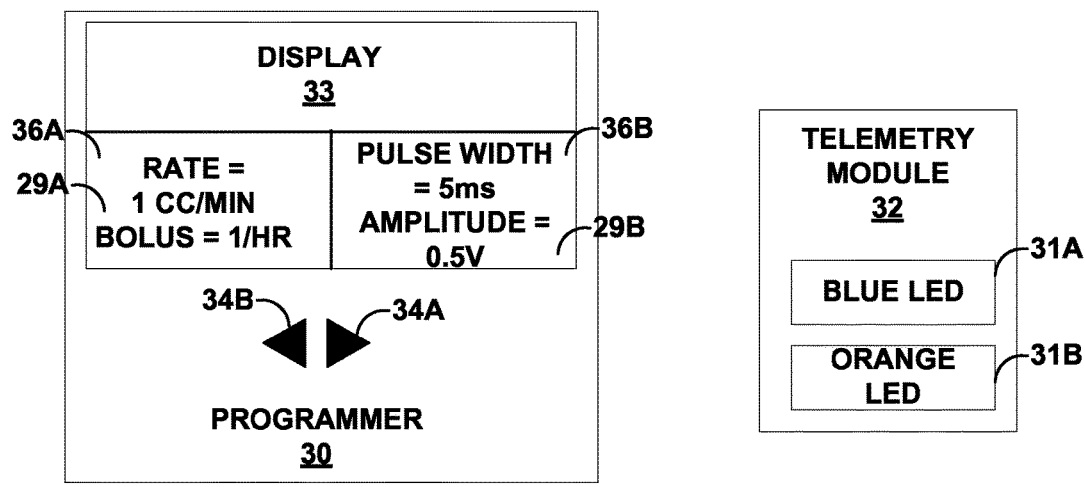

FIGS. 2A and 2B are conceptual diagrams illustrating example indications provided by an external programmer 30 and a telemetry module 32. In particular, FIGS. 2A and 2B illustrate an example in which the plurality of indications comprises a plurality of different colors. Programmer 30 and telemetry module 32 may be examples of programmer 20 and telemetry module 22, discussed above with reference to FIG. 1.

As shown in FIG. 2A, programmer 30 provides a blue display element 29A and an orange display element 29B (collectively "display elements 29"). Telemetry module 32 comprises a blue LED 31A and an orange LED 31B (collectively "LEDs 31"). In order to provide a substantially similar indication, telemetry module 32 may activate blue LED 31A when programmer 30 displays blue display element 29A, and orange LED 31B when programmer displays orange display element 29B. In this manner, programmer 30 and telemetry module 32 may indicate when they are coupled, e.g., bonded and/or communicating. Furthermore, the selection of which color of LEDs 31 and display elements 29 is active by the programmer and telemetry module may depend upon, for example with which IMD they are communicating, which therapy is being programmed, or which application is being used by programmer 30, as described above.

The color scheme of blue and orange is only chosen for the purpose of providing an example. Different examples may have different color schemes.

FIG. 2B further illustrates display elements 29 according to one example. As illustrated in FIG. 2B, programmer 30 may comprise a display 33. Display 33 may comprise, for example, a liquid crystal display (LCD), or other type of display. In some examples, display 33 comprise a touch screen display. As illustrated in FIG. 2B, the user interface provided by programmer 30 may also include buttons, such as scrolling arrows 34A and 34B, a touch pad, increase and decrease buttons, emergency shut off button, and other input media for interacting with programmer 30 and, through the programmer, an IMD, e.g., to control or program delivery of one or more therapies by the IMD.

In the illustrated example, display 33 presents two windows 36A and 36B (collectively "windows 36"). Window 36A facilitates interaction with a first IMD, e.g., IMD 14A, and window 36B facilitates interaction with a second IMD, e.g., IMD 14B. Window 36A displays parameters for the first IMD, which comprises a pump, and window 36B displays parameters for a second IMD, which comprises an electrical stimulator. Different examples may have more or fewer windows for programming more or fewer IMDs. In some examples, a single IMD provides multiple therapies associated with different windows.

In the illustrated example, programmer 30 may provide display elements 29 as colored borders or backgrounds for windows 36, each of orange and blue used for a respective one of windows 36. Telemetry module 32 may select which of LEDs 31 to activate based on which of windows 36 is currently being interacted with by a user. In some examples, windows 36 are not displayed at the same time. For example, windows 36 may be opened, closed, minimized, or maximized. In other examples, programmer 30 may provide different colored display elements 30 by coloring a background of display 33, or displaying a colored icon, depending on which window is open, maximized, or otherwise selected.

While FIGS. 2A and 2B describe indications 29 and 31 as visual indications, the disclosure is not so limited. For example, the indications may additionally or alternatively comprise audio or tactile indications, which may be substantially similar as between a programmer or a telemetry module. The indications may comprise a plurality of frequencies, or a spatial or temporal pattern. In some examples, indicators 19 may provide a vocal statement, which may name an IMD, therapy, or user, for example. The statement may be recorded by a user. A combination of different types of indications may be used at the same time or different times by the devices described herein.

Figure 3:
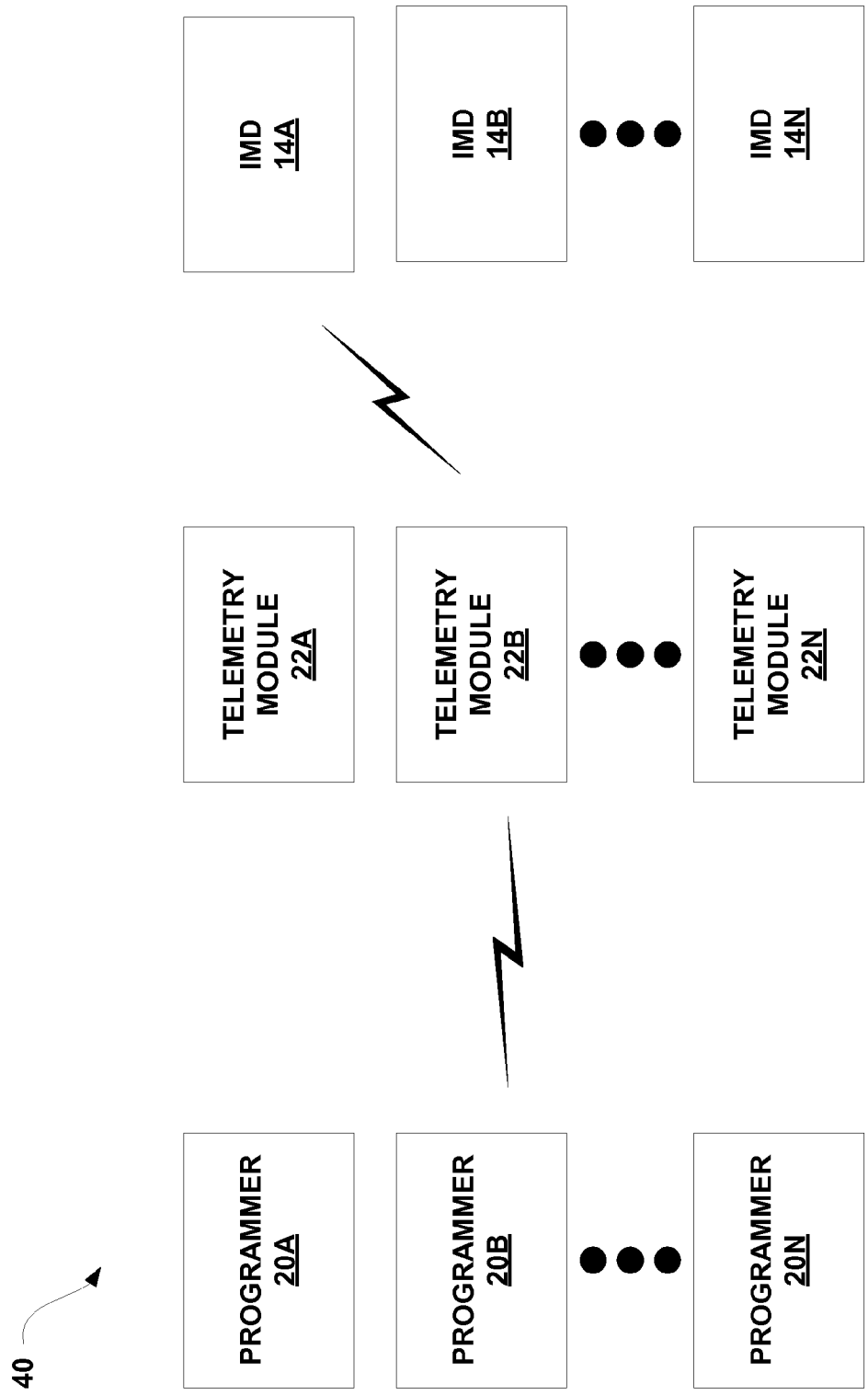
FIG. 3 is a conceptual diagram illustrating an example environment in which coupling indications may be provided.

FIG. 3 is a block diagram illustrating an example environment 40 in which the coupling indication techniques described herein may be implemented. Environment 40 comprises a plurality of programmers 20A-N, telemetry modules 22A-N and IMDs 14A-N. FIG. 3 illustrates that programmer 20B is coupled to telemetry module 22B for communication with IMD 14A. Programmer 20B and telemetry module 22B may provide a substantially similar indication, which may be associated with IMD 14A. In this manner, a user may determine with which of IMDs 14 he or she is communicating, as well as which of programmers 20 and telemetry modules 22 is used to communicate with that IMD.

In some examples, a different one of telemetry modules 22 may be required in order to communicate with a different one of IMDs 14. In such examples, selection of a different IMD via programmer 20B may cause programmer 20B and another telemetry module to provide a different indication associated with the other of IMDs 14. Similarly, use of a different programmer 20 with telemetry module 22B may cause the telemetry module to provide a different indication to indicate coupling of the telemetry module with the different programmer. Providing coupling indications according to this disclosure may help a user identify the devices with which he or she is communicating, as well as identifying which of a plurality of devices or applications is necessary for a desired communication session.

Figure 4:
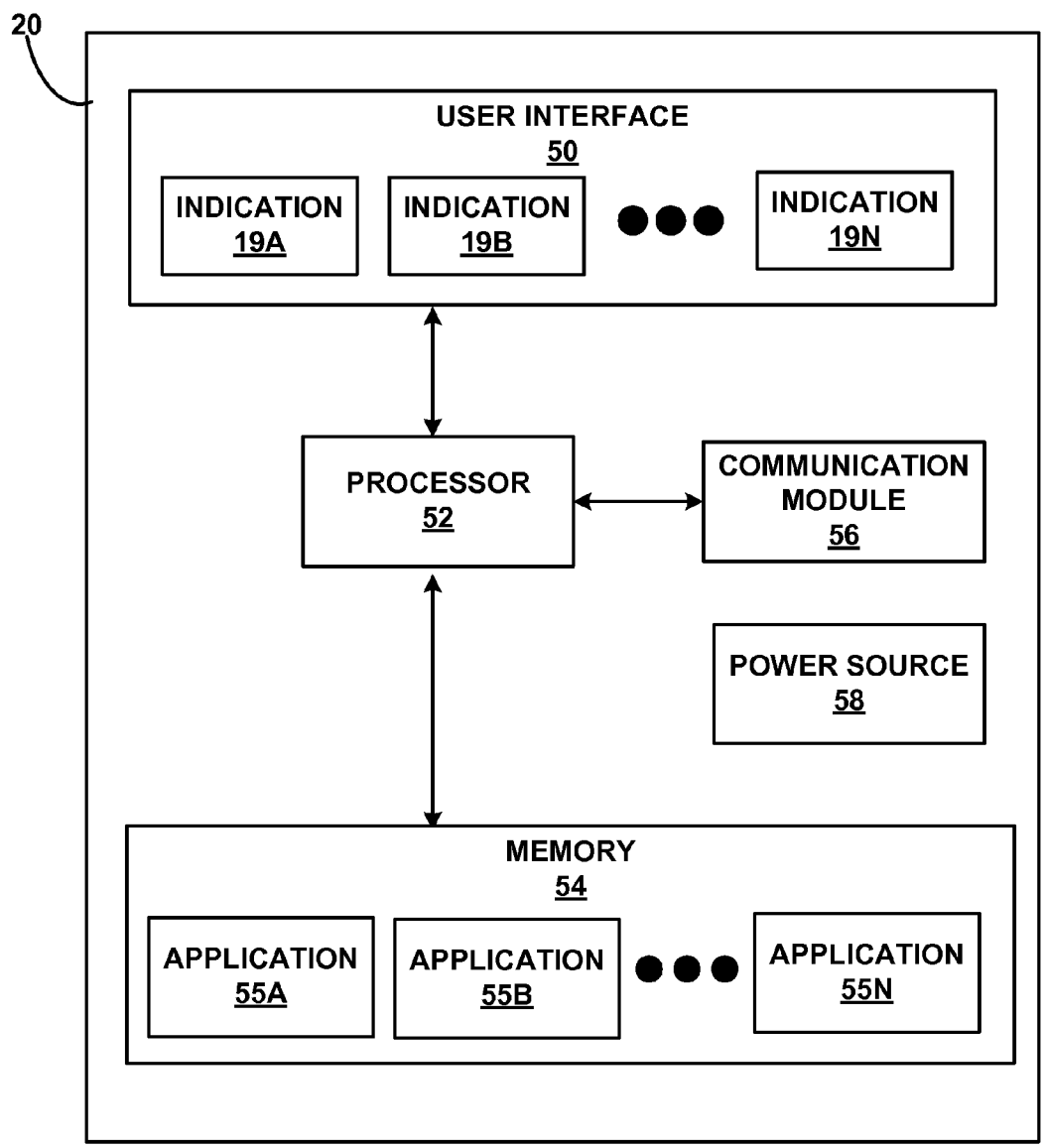
FIG. 4 is a functional block diagram illustrating an example programming device.

FIG. 4 is a functional block diagram illustrating a various components of programmer 20. As shown in FIG. 4, external programmer 20 includes user interface 50, processor 52, memory 54, communication module 56, and power source 58. User interface 50 may comprise a display and input media, as described above with respect to programmer 20. User interface provides a plurality of indications 19A-19N, which may comprises different colored display elements, as described herein. In some examples, user interface may comprise a vibrating element, speaker, lights, or the like to provide other types of indications described herein, as well as a microphone for user voice recordings used as an indicator.

Processor 52 may select which of indications 19 to provide at any given time, and may control the provision of the selected indication(s) by user interface 50. Processor 52 may select indications 19 based on information stored in memory 54, which may include information associating the indications with different telemetry modules 22, IMDs 14, therapies, or ones of applications 55A-55N (collectively "applications 55"), which are also stored in memory 54. Applications 55 may comprise different applications or software modules used to communicate with different IMDs 14. A plurality of applications 55 may be used to communicate with the same IMD 14 for different purposes, in some examples. Execution of or interaction with applications 55 may cause processor 52 to select an indication 19 associated with the application. In some examples, the association of an application 55 with an indication 19 may be stored as data for that application, and configured by interaction with that application.

Communication module 56 may comprise circuitry for wired or wireless communication (e.g., Bluetooth or IRDA) with one or more telemetry modules 22. Processor 52 may control identification of telemetry modules 22 in communication range, as well as bonding with the telemetry modules (if necessary), and communication with the telemetry modules. Bonding to provide secure and reliable communication is described in greater detail in co-pending and commonly-assigned U.S. application Ser. No. 11/800,423, filed May 4, 2007, entitled "INTELLIGENT DISCOVERY OF MEDICAL DEVICES BY A PROGRAMMING SYSTEM," which is incorporated herein by reference in its entirety.

Based on selection of an indication 19, processor 52 may provide information or an indication to a telemetry module 22 via communication module 46 that causes the telemetry module to provide a substantially similar indication 21.

Processor 52 may comprises a microprocessor, application specific integrated circuit (ASIC), field programmable gate array (FPGA), or any digital or analog logic circuitry. Memory 54 may comprise random access memory (RAM), read-only memory (ROM), CD-ROM, hard disk, flash memory, or other type of memory.

Power source 48 may be a rechargeable battery, such as a lithium ion or nickel metal hydride battery. Other rechargeable or conventional batteries may also be used. In some cases, external programmer 20 may be used when coupled to an alternating current (AC) outlet, i.e., AC line power, either directly or via an AC/DC adapter.

Figure 5:
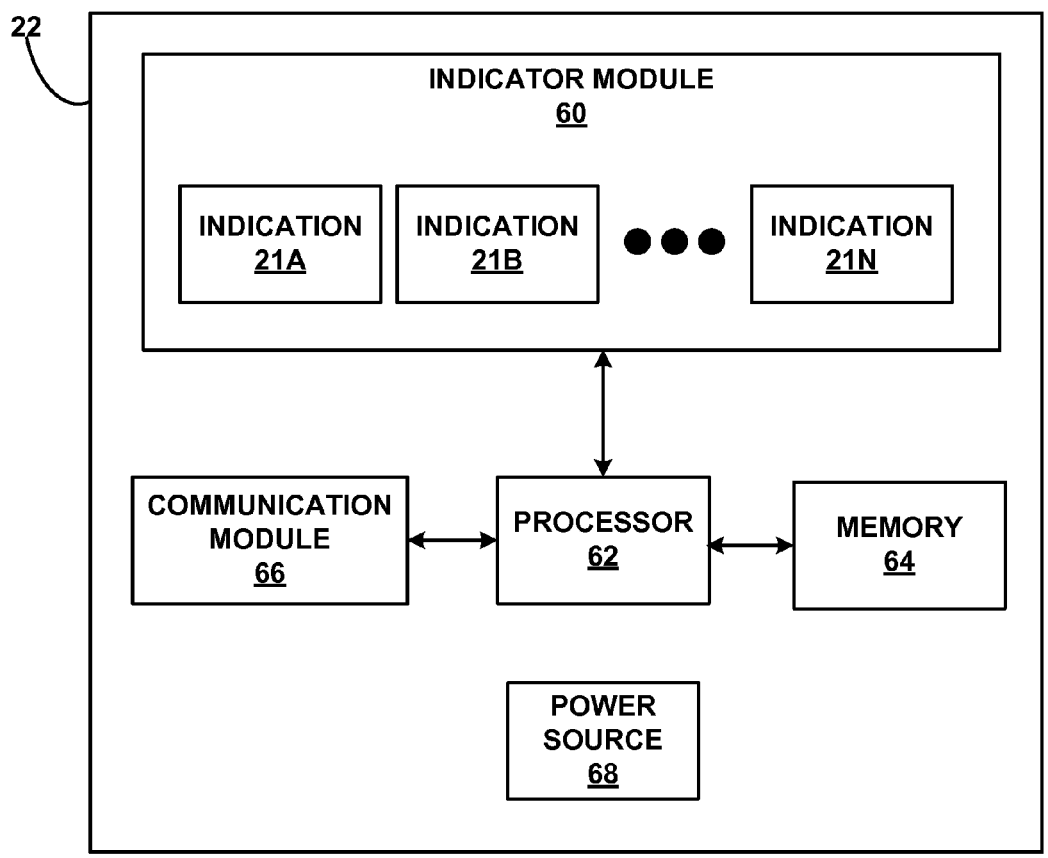
FIG. 5 is a functional block diagram illustrating an example telemetry module.

FIG. 5 is a functional block diagram illustrating components of an example telemetry module 22. Telemetry module 22 includes an indicator module 60, processor 62, memory 64, communication module 66 and power source 68. Indicator module 60 may comprise, for example, lights, which may be colored, speakers, or vibrating elements to provide a plurality of different indications 21.

Processor 62 may select which of indications 21 to provide at any given time, and may control the provision of the selected indication(s) by indicator module 60. Processor 62 may select indications 21 based on information stored in memory 64 and/or information received from a programmer 20 via communication module. For example, memory 64 may store associations between certain information received from programmer when attempting to communicate with different IMDs 14 with different indications 21, and select an indication 21 based on receipt of such information.

Communication module 66 may comprise circuitry for wired or wireless communication with programming devices 20, as well as circuitry for transcutaneous communication, e.g., magnetic or radio-frequency, with one or more IMDs 14. Processor 62 may control identification of programmers 20 or IMDs 14 in communication range, as well as bonding with the programmers or IMDs (if necessary), and communication with the programmer and IMDs. Processor 62 may comprises a microprocessor, application specific integrated circuit (ASIC), field programmable gate array (FPGA), or any digital or analog logic circuitry. Memory 64 may comprise random access memory (RAM), read-only memory (ROM), CD-ROM, hard disk, flash memory, or other type of memory.

Power source 66 may be a rechargeable battery, such as a lithium ion or nickel metal hydride battery. Other rechargeable or conventional batteries may also be used. In some cases, telemetry module 22 may be used when coupled to an alternating current (AC) outlet, i.e., AC line power, either directly or via an AC/DC adapter.

Figure 6:
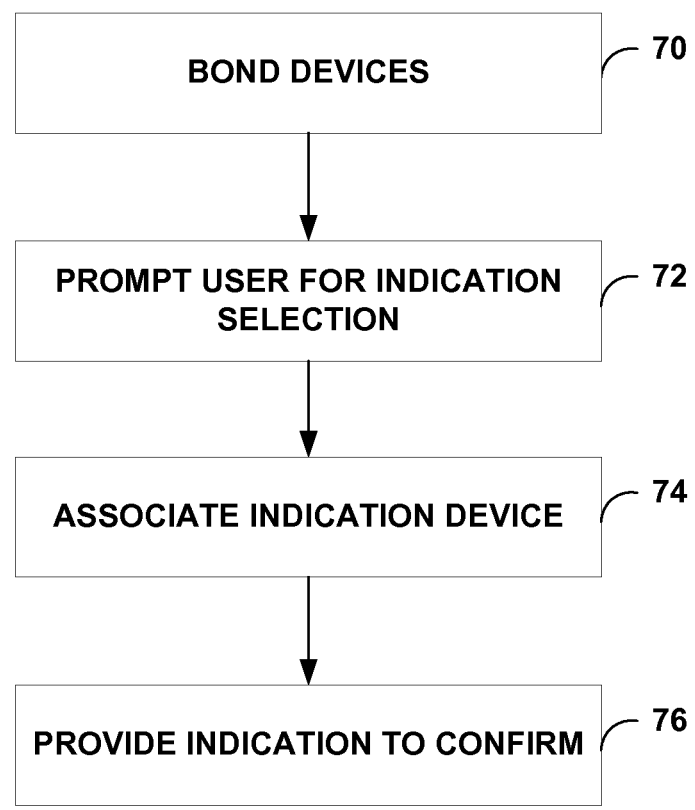
FIG. 6 is flow diagram illustrating an example technique for associating a coupling indication with a bonded device.

FIG. 6 is flow diagram illustrating an example technique for associating coupling indications with a bonded device. The example technique of FIG. 6 may be performed by one or both of a programming device or telemetry module when bonding with each other and/or an IMD.

According to the illustrated example, two or more devices are bonded (70). One of the devices, e.g., a programming device, prompts a user to select indication scheme for the bonded devices (72). The devices associate indications with each other (74), and provide the indications to confirm the bonding (76).

For example, a user may wish to communicate with a particular IMD to program a particular therapy for a first time. Using a programming device, the user may open an appropriate application for communicating with the IMD. If the programming device is not bonded to a telemetry head, and the telemetry head is not bonded to the IMD, the application may facilitate the bonding process. The application may also prompt the user to select an indication scheme for communication using this combination of devices with the application. Based on the users input, information regarding the association of an indication with this combination may be communicated to the telemetry module and stored in the devices respective memories so that the selected indications may be provided in the future.

The selected indications may be user specific. Different users may have different indication schemes for the same combinations of devices and applications. In this manner, a user may discern whether the devices are otherwise configured according to their preferences based on the indications provided by a programming device and telemetry module.

The selected indications may be provided to confirm the selection and the bonding of the devices. The confirmation indication may be more brief and of a different character than the indication later used during communication sessions. For example, the communication indication may be colored lights or display elements active substantially throughout the communication session, while the confirmation or bonding indication may be a relatively short pattern of flashing lights or display elements in the selected color.

Figure 7:
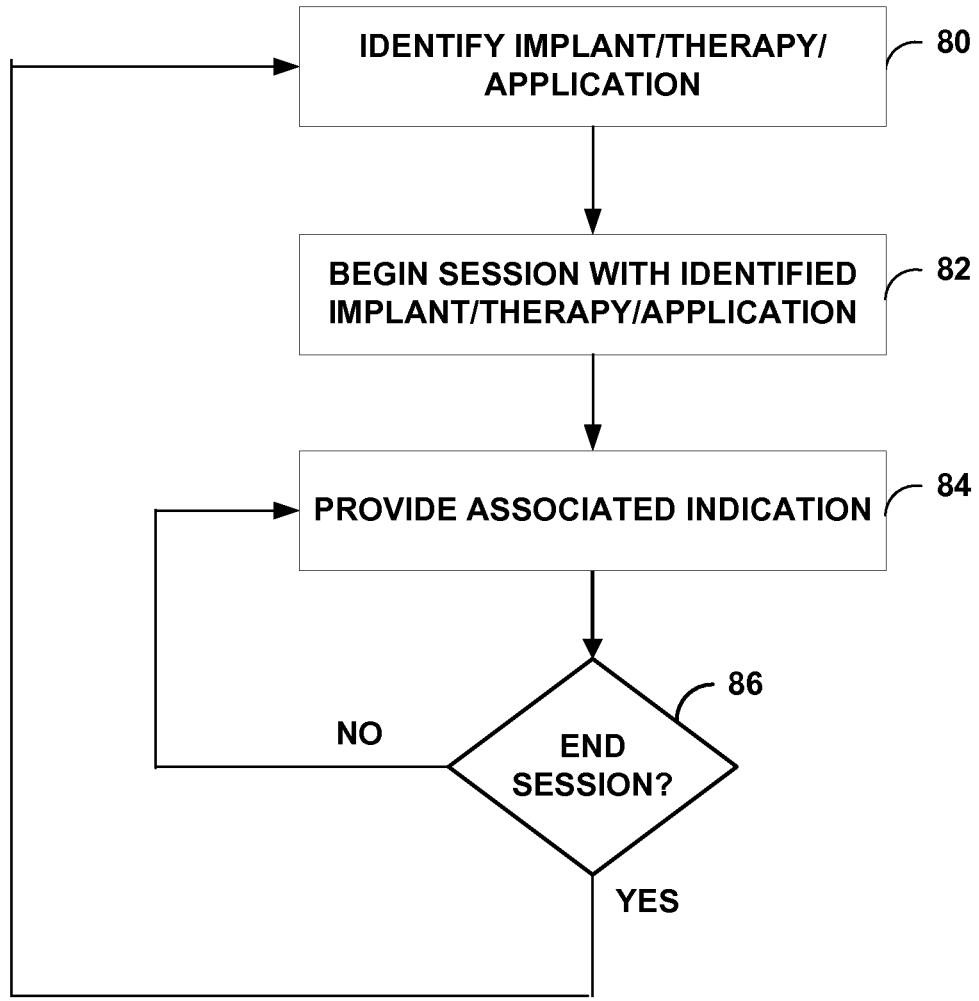
FIG. 7 is a flow diagram illustrating an example technique for providing associated indications during communication sessions.

FIG. 7 is a flow diagram illustrating an example technique for providing associated indications during communication sessions. The technique of FIG. 7 may be practiced by one or both of a programming device and a telemetry module.

According to the illustrated example, the current implant, therapy, and/or application is identified (80), e.g., based on user selection or activation via the programming device. A communication session involving the identified element(s) is initiated (82) using the programming device and the telemetry module. Indications associated with the identified element(s) are provided by the programming device and telemetry module (84). The indications may be provided substantially throughout the session, or periodically during the session, as examples. If the session is ended (86), e.g., by the user, the devices may stop providing the associated indication. A new session with a different indication may be started using the same technique.

As another example, in step 84, the indication may alternatively or additionally be provided by the implantable medical device. For instance, such an indication may be provided using sound and/or vibration. Providing an indication by an implantable medical device is discussed further below.

FIG. 8 is a schematic diagram illustrating an example telemetry module 90. Telemetry module 90 includes a plurality of lights 92A-92D (collectively "lights 92"), which may be LEDs. Lights 92 are located on or within different portions of telemetry module 90. The number and locations of lights 92 is merely an example.

Two or more of lights 92 may be associated with respective IMDs 14 implanted within a patient 12. More particularly, lights 92 may be associated with IMDs whose position within the patient corresponds to their location on or within telemetry module 90. In this manner, illumination of one of lights 92 indicates coupling, e.g., bonding or communication, with an IMD implanted in the patient at location corresponding to the location of the light 92 on or within the telemetry module 90. The user may be familiar with the location of one or more IMDs within the patient in such examples. For example, Lights 92C and 92B may respectively be used to indicate coupling with IMDs 14A and 14B (FIG. 1). Programming devices may also indicate coupling with an IMD by locating an indication in a manner that corresponds to an implant location of the IMD.

Figure 9A:
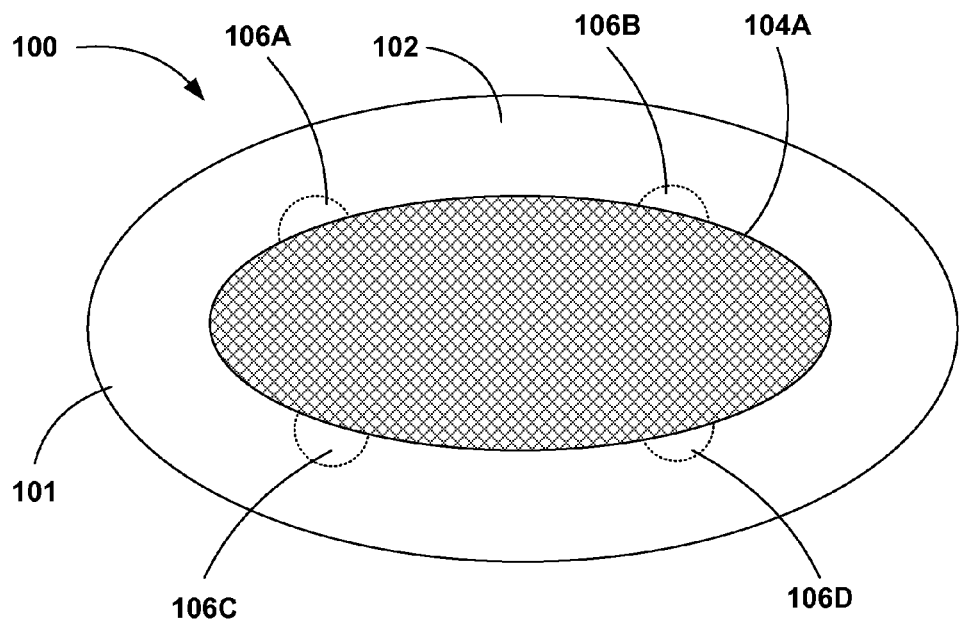
FIGS. 9A and 9B are respectively top and side views of an example telemetry module with an at least partially translucent housing.
Figure 9B:
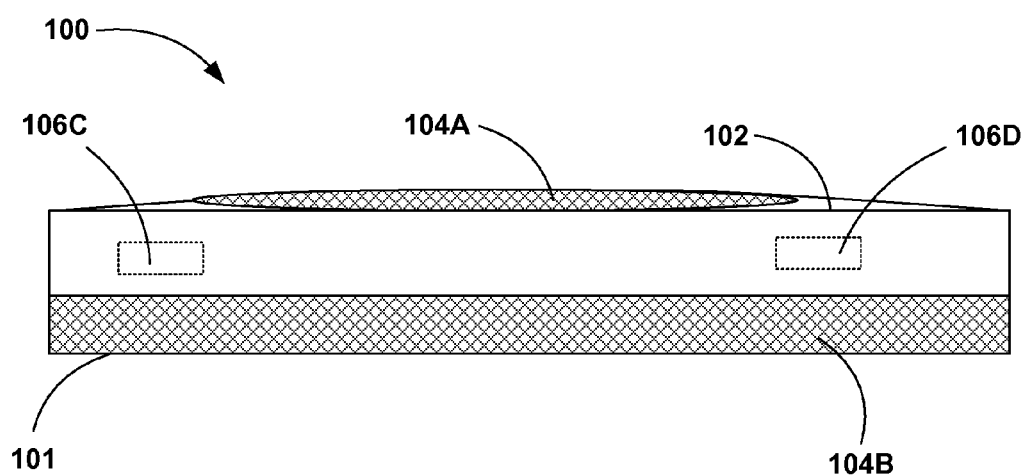

FIGS. 9A and 9B are respectively top and side views of an example telemetry module 100 with an at least partially translucent housing 101. Housing 101 includes translucent portion 102 and substantially opaque portions 104A and 104B. Translucent portion 102 may be part of a non-display portion of housing 101, i.e., translucent portion 102 does not include a display, to the extent telemetry module 100 comprises a display. Translucent portion 102 may comprise at least approximately ten percent, at least approximately 20 percent, or at least approximately 50 percent of a non-display portion of the housing. In some examples, greater than 85 percent, or substantially all of the entire non-display portion of housing 101 may be translucent. Translucent portion 102 may be located on a periphery of housing 101, as illustrated in FIG. 9A.

FIGS. 9A and 9B also illustrated a plurality of lights 106A-106D (collectively "lights 106"), which may be LEDs, within housing 101. The locations and number of lights is merely an example. Lights 106 may provide indications, e.g., colored indications, as described herein. Translucent portion 102 may allow a user to see light emitted by lights 106. Emission of colored light through translucent portion 102 may be perceived by the user as "coloring" telemetry module 100, which may provide a clear and easily perceivable indication 21. In some examples, telemetry module 100 includes at least three lights and/or provides at least three different colors, e.g., for different indications 21.

Figure 10A:
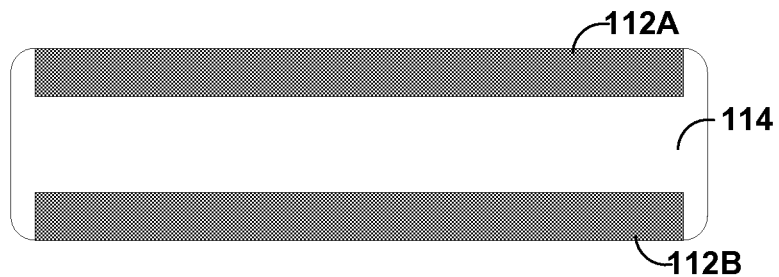
FIGS. 10A and 10B are schematic diagrams illustrating an example of a detachable physical indication placed on a telemetry module.
Figure 10B:
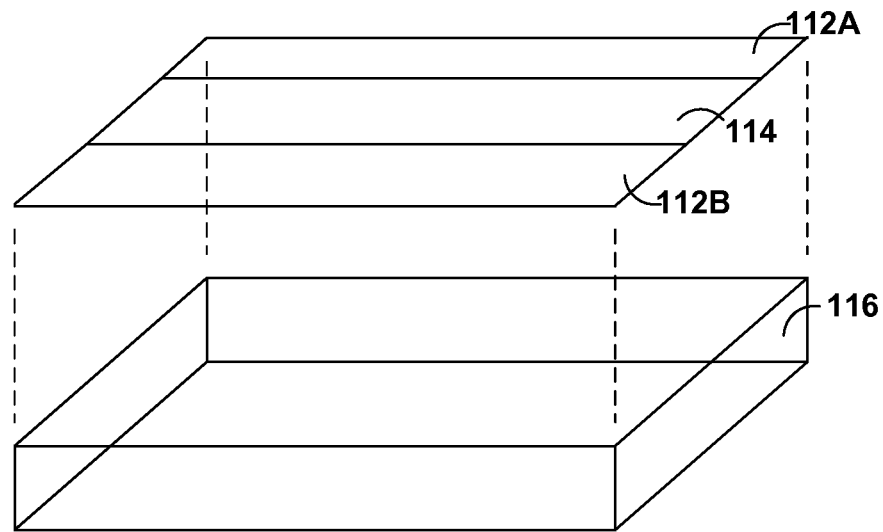

FIGS. 10A and 10B are side and perspective views illustrating an example of a detachable physical indication 114 placed on a telemetry module 116. Telemetry module 116 may be substantially similar to telemetry module 22 or other telemetry modules described herein.

A user may attach indication 114 to telemetry module 116 to indicate the bonding of telemetry module to one or more other devices, in a similar manner described herein with respect to other indications. Indication 114 comprises colored sections 112A and 112B. Different indications 114 with different colors for sections 112A and 112B may be attached or detached to indicate, e.g., by a user to remind themselves, to which device(s) the telemetry modules are coupled, e.g., bonded to or communicating with. The location, number and size of sections 112A and 112B are merely an example.

The techniques described in this disclosure, including those attributed to processors 42, 52, and 60 or various constituent components, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, stimulators, or other devices. The term "processor" or "processing circuitry" may generally refer to any of the foregoing logic circuitry, alone or in combination with other logic circuitry, or any other equivalent circuitry.

Such hardware, software, firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable storage medium such as RAM, ROM, NVRAM, EEPROM, FLASH memory, magnetic data storage media, optical data storage media, or the like. The instructions may be executed to support one or more aspects of the functionality described in this disclosure.

Various examples have been described in this disclosure. However, a person of ordinary skill will appreciate that various modifications may be made to the described examples. For example, although described primarily in the context of indications provided by programming devices and telemetry modules, IMDs may also provide indications that, in some cases, may be substantially similar to those provided by a coupled programming device and telemetry module. Similar sounds or vibrations may be provided by an IMD, for example. Furthermore, in some examples, the IMD may provide a pager like beeping or vibration in response to a request from a user using a programming device to confirm or indicate its coupling to the system.

The invention claimed is:

1. A system comprising:
an external telemetry module that is configured to transcutaneously communicate with a plurality of implantable medical devices (IMDs); and
an external programming device that is configured to:
communicate with the telemetry module and with each of the plurality of IMDs through the telemetry module;
present, via a user interface, a plurality of indication schemes; and
receive, via the user interface, a selection of an indication scheme from the plurality of indication schemes,
wherein the external telemetry module is configured to provide a first plurality of different indications of coupling, each of the first plurality of indications associated with a respective one of the plurality of IMDs, and wherein, in response to transcutaneously communicating with one of the plurality of IMDs, the external telemetry module is configured to:
select one of the first plurality of indications associated with the one of the plurality of IMDs; and
provide the selected one of the first plurality of indications,
wherein the external programming device is configured to provide a second plurality of different indications of coupling, each of the second plurality of indications associated with the respective one of the plurality of IMDs and substantially similar to a corresponding one of the first plurality of indications, and wherein, in response to communicating with the one of the plurality of IMDs though the telemetry module, the external programming device is configured to:
select one of the second plurality of indications associated with the one of the plurality of IMDs based on the selected indication scheme from the plurality of indication schemes; and
provide the selected one of the second plurality of indications,
wherein the selected one of the second plurality of indications is substantially similar to the selected one of the first plurality of indications.

2. The system of claim 1, wherein the first plurality of indications and the second plurality of indications comprise first and second sets of colors that are at least substantially similar, wherein the selected one of the first plurality of indications comprises a selected one of the first set of colors and the selected one of the second plurality of indications comprises a selected one of the second set of colors, and wherein the selected ones of the first and second sets of colors comprise substantially similar colors.

3. The system of claim 2,
wherein the telemetry module comprises at least one light that provides a selected one of the first plurality of colors, and
wherein the programming device comprises a display that provides a selected one of the second plurality of colors that is at least substantially similar to the selected one of the first plurality of colors.

4. The system of claim 3, wherein the display presents at least one of a background, an application window, or an icon in the selected one of the second plurality of colors.

5. The system of claim 1, wherein the first plurality of indications and the second plurality of indications comprise audible indications that are at least substantially similar.

6. The system of claim 1, wherein the first plurality of indications and the second plurality of indications comprise patterns that are at least substantially similar, wherein the patterns are at least one of spatial or temporal and comprise light.

7. The system of claim 1, wherein the external telemetry module and the external programming device provide the first plurality of indications and the second plurality of indications substantially continuously throughout a session in which the external telemetry module and the external programming device communicate.

8. The system of claim 1,
wherein at least some of the first plurality of indications and the second plurality of indications are associated with respective ones of a plurality of therapies, and
wherein the external telemetry module and the external programming device respectively select one of the first plurality of indications and one of the second plurality of indications based on a therapy delivered by the one of the plurality of IMDs.

9. The system of claim 1,
wherein at least some of the first plurality of indications and the second plurality of indications are associated with respective ones of a plurality of applications executable by the external programming device for communication with the plurality of IMDs, and
wherein the external telemetry module and the external programming device respectively select one of the first plurality of indications and one of the second plurality of indications based on which application of the plurality of applications is currently selected.

10. The system of claim 1,
wherein at least two IMDs of the plurality of IMDs are implanted within a patient,
wherein the first plurality of indications comprises visual indications, and
wherein the external telemetry module is configured to provide the first plurality of indications at a plurality of locations on or within the external telemetry module, each of the plurality of locations on or within the external telemetry module corresponding to a location of a respective one of the at least two IMDs within the patient, to indicate with which of the at least two IMDs the external telemetry module is coupled.

11. The system of claim 1, wherein the external telemetry module is wirelessly coupled to the external programming device.

12. The system of claim 1, further comprising an IMD of the plurality of IMDs,
wherein, when coupled to at least one of the external telemetry module or the external programming device, the IMD provides a third indication of coupling.

13. The system of claim 12, wherein the third indication is substantially similar to the selected one of the first plurality of indications and the selected one of the second plurality of indications.

14. A method for indicating coupling between an external telemetry module that is configured to transcutaneously communicate with a plurality of implantable medical devices (IMDs) and an external programming device that is configured to communicate with the telemetry module and with each of the plurality of IMDs through the telemetry module, the method comprising:
presenting, via a user interface of the external programming device, a plurality of indication schemes;
receiving, via the user interface, a selection of an indication scheme from the plurality of indication schemes;
in response to transcutaneously communicating, by the external telemetry module, with one of the plurality of IMDs:
selecting, by the external telemetry module and based on the selected indication scheme from the plurality of indication schemes, one of a first plurality of different indications of coupling, wherein each of the first plurality of indications is associated with a respective one of the plurality of IMDs; and
providing, by the external telemetry module and to the user, the selected one of the first plurality of indications; and
in response to communicating, by the external programming device, with the one of the plurality of IMDs though the telemetry module:
selecting, by the external programming device, one of a second plurality of indications of coupling, wherein each of the second plurality of indications is associated with a respective one of the plurality of IMDs; and
providing, by the external programming device and to the user, the selected one of the second plurality of indications, wherein the selected one of the second plurality of indications is substantially similar to the selected one of the first plurality of indications.

15. The method of claim 14, wherein the first plurality of indications and the second plurality of indications comprise first and second sets of colors that are at least substantially similar, wherein the selected one of the first plurality of indications comprises a selected one of the first set of colors and the selected one of the second plurality of indications comprises a selected one of the second set of colors, and wherein the selected ones of the first and second sets of colors comprise substantially similar colors.

16. The method of claim 14, further comprising selecting the one of the first plurality of indications and selecting the one of the second plurality of indications based on selection of at least one of:
the one IMD device from among of the plurality of IMDs, a therapy from among a plurality of therapies, or an application for programming the one IMD from among a plurality of applications.

17. A system comprising:
means for transcutaneously communicating with a plurality of implantable medical devices (IMDs); and
external programming means for communicating with each of the plurality of IMDs through the means for transcutaneously communicating, presenting, via a user interface, a plurality of indication schemes, and receiving, via the user interface, a selection of an indication scheme from the plurality of indication schemes;
wherein the means for transcutaneously communicating is configured to provide a first plurality of different indications of coupling, each of the first plurality of indications associated with a respective one of the plurality of IMDs, and wherein, in response to transcutaneously communicating with one of the plurality of IMDs, the means for transcutaneously communicating is configured to:
select one of the first plurality of indications associated with the one of the plurality of IMDs; and
provide the selected one of the first plurality of indications,
wherein the external programming means is configured to provide a second plurality of different indications of coupling, each of the second plurality of indications associated with the respective one of the plurality of IMDs and substantially similar to a corresponding one of the first plurality of indications, and wherein, in response to communicating with the one of the plurality of IMDs though the means for transcutaneously communicating, the external programming means is configured to:
select one of the second plurality of indications associated with the one of the plurality of IMDs based on the selected indication scheme from the plurality of indication schemes; and
provide the selected one of the second plurality of indications,
wherein the selected one of the second plurality of indications is substantially similar to the selected one of the first plurality of indications.

18. The system of claim 17, further comprising means for selecting the one of the first plurality of indications and selecting the one of the second plurality of indications based on selection of at least one of:
the one IMD device from among of the plurality of IMDs, a therapy from among a plurality of therapies, or an application for programming the one IMD from among a plurality of applications.

19. The system of claim 1, wherein the first plurality of indications and the second plurality of indications comprise tactile indications that are at least substantially similar.

20. The system of claim 1, wherein the first plurality of indications and the second plurality of indications comprise patterns of vibrations that are at least substantially similar.

21. The system of claim 1, wherein the first plurality of indications and the second plurality of indications comprise patterns that are at least substantially similar, wherein the patterns are spatial and comprise color.

22. The system of claim 1, wherein the first plurality of indications and the second plurality of indications comprise patterns that are at least substantially similar, wherein the patterns are spatial and comprise animation.

23. The system of claim 1, wherein the first plurality of indications and the second plurality of indications comprise patterns that are at least substantially similar, wherein the patterns are temporal and comprise sound.

24. The system of claim 1, wherein the first plurality of indications and the second plurality of indications comprise patterns that are at least substantially similar, wherein the patterns are temporal and comprise music.

25. The system of claim 1, wherein the first plurality of indications and the second plurality of indications comprise patterns that are at least substantially similar, wherein the patterns are temporal and comprise user voice recordings.

26. The system of claim 1,
wherein the first plurality of indications comprise a set of lights having a first set of colors,
wherein the second plurality of indications comprise at least one of a background, an application window, or an icon, the at least one of the background, the application window, or the icon having a second set of colors,
wherein the selected one of the first plurality of indications comprises a selected one of the set of lights having the first set of colors,
wherein the selected one of the second plurality of indications comprises a selected one of the at least one of the background, the application window, or the icon having the second set of colors, and
wherein the selected one of the set of lights having the first set of colors and the selected one of the at least one of the background, the application window, or the icon having the second set of colors comprise substantially similar colors.

27. The system of claim 1, wherein, to select the one of the first plurality of indications associated with the one of the plurality of IMDs, the external telemetry module is further configured to:
receive, from the external programming device, the selection of the indication scheme from the plurality of indication schemes; and
select the one of the first plurality of indications associated with the one of the plurality of IMDs based on the selected indication scheme from the plurality of indication schemes.

* * * * *